(12) United States Patent
Kurzweil et al.

(10) Patent No.: US 9,277,867 B2
(45) Date of Patent: Mar. 8, 2016

(54) GARMENT ACCESSORY WITH ELECTROCARDIOGRAM SENSORS

(71) Applicant: Medicomp, Inc., Melbourne, FL (US)

(72) Inventors: Raymond C. Kurzweil, Newton, MA (US); Paul Albrecht, Bedford, MA (US); Lucy Gibson, Belmont, MA (US); Amara Angelica, Webster, NY (US); Aaron Kleiner, West Newton, MA (US)

(73) Assignee: Medicomp, Inc., Melbourne, FL (US)

( * ) Notice: Subject to any disclaimer, the term of this patent is extended or adjusted under 35 U.S.C. 154(b) by 80 days.

(21) Appl. No.: 14/021,498

(22) Filed: Sep. 9, 2013

(65) Prior Publication Data

US 2014/0012145 A1 Jan. 9, 2014

Related U.S. Application Data

(62) Division of application No. 11/749,248, filed on May 16, 2007, now Pat. No. 8,560,044.

(51) Int. Cl.
| | |
|---|---|
| *A61B 5/0408* | (2006.01) |
| *A61B 5/0205* | (2006.01) |
| *A61B 5/00* | (2006.01) |
| *A61B 5/053* | (2006.01) |
| *A61B 5/01* | (2006.01) |

(52) U.S. Cl.
CPC ............ *A61B 5/0205* (2013.01); *A61B 5/01* (2013.01); *A61B 5/0408* (2013.01); *A61B 5/0535* (2013.01); *A61B 5/6804* (2013.01); *A61B 5/6805* (2013.01); *A61B 5/6823* (2013.01)

(58) Field of Classification Search
CPC ...... A61B 5/04; A61B 5/0402; A61B 5/0408; A61B 5/04085; A61B 5/6804; A61B 5/6805; A61B 5/6823; A61B 5/6831; A61B 2562/0209
USPC ................. 600/382, 388–390, 393, 509, 301; 450/1–93
See application file for complete search history.

(56) References Cited

U.S. PATENT DOCUMENTS

| | | | | |
|---|---|---|---|---|
| 3,830,224 | A | * | 8/1974 | Vanzetti et al. ............... 600/549 |
| 4,381,012 | A | | 4/1983 | Russek |
| 4,580,572 | A | * | 4/1986 | Granek et al. ................ 600/388 |
| 4,729,377 | A | * | 3/1988 | Granek et al. ................ 600/393 |

(Continued)

FOREIGN PATENT DOCUMENTS

| | | |
|---|---|---|
| CA | 2324713 | 4/2001 |
| GB | 2388196 | 11/2003 |

(Continued)

*Primary Examiner* — Lee S Cohen
*Assistant Examiner* — Erin M Cardinal
(74) *Attorney, Agent, or Firm* — Mark Malek; Kelly G. Swartz; Widerman Malek, PL

(57) ABSTRACT

The brassiere may include at least one accommodation disposed on a portion of the brassiere with the at least one accommodation configured to carry at least a pair of sensors. The pair of sensors may be detachably carried by the at least one accommodation. The accommodation may be a pocket, slit, or pouch. The accommodation may be a pair of pockets that support a garment accessory. The garment accessory may include a member having first and second ends that fit within the pair of pockets. The pair of sensors may be carried by the member, which holds the sensors against the skin of a subject wearing the brassiere. The garment accessory may further include a wireless transmitter carried by the member.

18 Claims, 15 Drawing Sheets

(56) References Cited

U.S. PATENT DOCUMENTS

| | | | |
|---|---|---|---|
| 5,353,793 A | 10/1994 | Bornn | |
| 5,445,149 A | 8/1995 | Rotolo et al. | |
| 5,611,085 A * | 3/1997 | Rasmussen | 2/102 |
| 6,047,203 A | 4/2000 | Sackner et al. | |
| 6,102,856 A | 8/2000 | Groff et al. | |
| 6,205,346 B1 | 3/2001 | Akiva | |
| 6,341,504 B1 | 1/2002 | Istook | |
| 6,428,490 B1 * | 8/2002 | Kramer et al. | 600/595 |
| 6,477,397 B1 | 11/2002 | Ronkainen et al. | |
| 6,551,252 B2 | 4/2003 | Sackner et al. | |
| 6,571,115 B2 * | 5/2003 | Axelgaard et al. | 600/388 |
| 6,668,380 B2 | 12/2003 | Marmaropoulos et al. | |
| 6,755,795 B2 | 6/2004 | Marmaropoulos et al. | |
| 6,807,438 B1 | 10/2004 | Brun Del Re et al. | |
| 6,912,414 B2 | 6/2005 | Tong | |
| 6,930,608 B2 | 8/2005 | Grajales et al. | |
| 7,173,437 B2 | 2/2007 | Hervieux | |
| 7,308,294 B2 | 12/2007 | Hassonjee | |
| 7,330,751 B2 | 2/2008 | Ueda | |
| 7,670,295 B2 | 3/2010 | Sackner | |
| 8,224,418 B2 | 7/2012 | Birnbaum | |
| 8,560,044 B2 * | 10/2013 | Kurzweil et al. | 600/386 |
| 2003/0212319 A1 | 11/2003 | Magill | |
| 2004/0073104 A1 * | 4/2004 | Brun del Re et al. | 600/372 |
| 2005/0010096 A1 * | 1/2005 | Blackadar | 600/388 |
| 2005/0043641 A1 * | 2/2005 | Ueda | 600/509 |
| 2005/0049515 A1 | 3/2005 | Misczynski | |
| 2005/0059896 A1 | 3/2005 | Drakulic | |
| 2005/0119701 A1 | 6/2005 | Lauter | |
| 2005/0228234 A1 | 10/2005 | Yang | |
| 2005/0261564 A1 * | 11/2005 | Ryu et al. | 600/388 |
| 2005/0275416 A1 * | 12/2005 | Hervieux et al. | 324/663 |
| 2006/0069320 A1 | 3/2006 | Wolf | |
| 2006/0135863 A1 * | 6/2006 | Birnbaum et al. | 600/388 |
| 2007/0073131 A1 * | 3/2007 | Ryu et al. | 600/388 |
| 2008/0287769 A1 | 11/2008 | Kurzweil et al. | |
| 2009/0088652 A1 * | 4/2009 | Tremblay | 600/509 |
| 2010/0191090 A1 * | 7/2010 | Shin et al. | 600/388 |
| 2010/0324405 A1 * | 12/2010 | Niemi et al. | 600/396 |

FOREIGN PATENT DOCUMENTS

| | | |
|---|---|---|
| WO | WO02030279 | 4/2002 |
| WO | WO2005053532 | 6/2005 |
| WO | WO2006111875 A1 | 10/2006 |

* cited by examiner

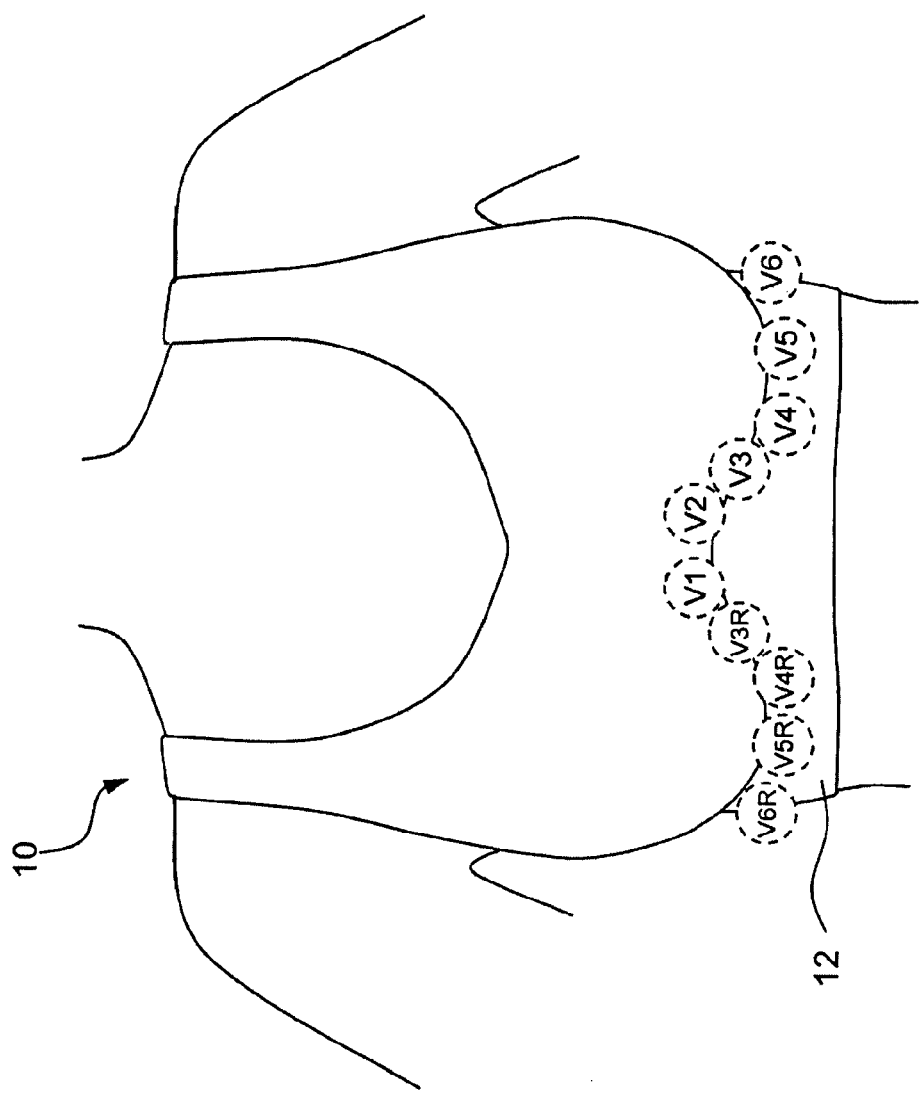

GARMENT ACCESSORY WITH ELECTROCARDIOGRAM SENSORS

CROSS-REFERENCE TO RELATED APPLICATIONS

The present application is a divisional of U.S. patent application Ser. No. 11/749,248 titled Garment Accessory with Electrocardiogram Sensors filed on 16 May, 2007, now U.S. Pat. No. 8,560,044 issued Oct. 15, 2013, the entire contents of which are incorporated herein by reference.

BACKGROUND OF THE INVENTION

The present invention relates to electrocardiogram (EGG) monitoring, and in particular to a wearable device with integrated ECG sensors for ambulatory ECG monitoring.

Heart disease is a leading cause of death in the United States. Some patients would benefit from long-term ECG monitoring outside of a clinical setting. For example, atrial fibrillation and myocardial ischemia may occur episodically. Some episodes may occur without patient symptoms. Myocardial ischemia, if persistent and serious, can lead to myocardial infarction (heart attack). During a myocardial infarction, electrophysiological changes are usually seen on the ECG. For accurate diagnosis and effective treatment of many episodic heart conditions, it is useful to know the frequency and duration of such episodes, in a timely manner.

In conventional long-term ECG monitoring, such as with continuous Holter monitors or event monitors, the skin is prepared by a technician. Chest hair may be shaved or clipped from men. The skin is abraded to remove dead skin cells, and cleaned. Abrading often leaves the skin irritated. A technician trained in electrode placement applies the electrodes to the skin with an adhesive. The monitor can be worn for up to a month.

Each electrode of such conventional monitors is attached to an insulated wire that is routed to an amplifier to amplify the ECG signal. The patient has to take care not to pull on the wires connected to the electrode, because the electrode could be pulled off the skin. Removing the electrode with its strong adhesive may be painful. Many electrodes also use a gel next to the skin to improve conductivity of connection of the metal electrode to the skin. Prolonged exposure to the gel can irritate the skin.

SUMMARY OF THE INVENTION

The present invention has been made to solve the problems described above. The brassiere (also referred to as a bra) according to an embodiment of the present invention advantageously contours to the torso of the patient and enables sensors to be attached to the brassiere. Another benefit of the present invention is that the sensor is lightweight and may contact the subject without causing the patient to feel any pressure, discomfort or tightness.

These and other features and advantages according to an embodiment of the present invention are provided by the brassiere. The brassiere may include at least one accommodation disposed on a portion of the brassiere with the at least one accommodation configured to carry at least a pair of sensors. The pair of sensors may be detachably carried by the at least one accommodation. The accommodation may be a pocket, slit, or pouch.

The accommodation may be a pair of pockets that support a garment accessory. The garment accessory may include a member having first and second ends that fit within the pair of pockets. A pair of sensors may be carried by the member which holds the sensors against the skin of a subject wearing the brassiere. The garment accessory may further include a wireless transmitter carried by the member.

The accommodation in the brassiere may be a pouch formed by a layer of material coupled to a portion of the brassiere. The pouch may include an opening in a portion of the material facing the user's body so that at least one of the pair of sensors may make contact with the skin of a subject wearing the brassiere. The accommodation may be a pouch formed by a layer of material coupled to a portion of the brassiere. The pouch may be configured to be closed so that at least a portion of the pouch that faces the wearer's body may house a capacitively-coupled removable sensor.

The accommodation may be a plurality of loops of material disposed on a strap portion of the brassiere to support a member carrying at least one of the pair of sensors. The accommodation may also be a slit through a portion of the brassiere through which a portion of at least one of the pair of sensors may be supported. A portion of the sensor may be on a skin side of the slit and a separate portion of the sensor may overlap the portion of the brassiere and be on an opposing side of the slit. Furthermore, the accommodation may be a slot, groove, clip or re-closable fastener capable of carrying wiring.

The brassiere may include the pair of sensors which are at least one of ECG sensors, motion sensors, body temperature sensors or impedance plethysmography sensors. The pair of sensors may include sensor membranes configured to rest against the skin of a wearer of the brassiere. The sensor membranes may be in electrical contact with a mating snap and the sensor membranes may include an electrically conductive, flexible material. The sensor membranes may also have a major surface that is exposed to make contact with the skin of the wearer of the brassiere. The major surface may be curved or flat and may also be covered with a conductive gel film.

The pair of sensors may further comprise a sensor frame comprised of a firm, flexible material supporting the sensor membrane. The sensor membrane may also include a sensor membrane that comprises a water resistant material to induce sweat.

One or more aspects of the present invention may provide one or more of the following advantages.

Some embodiments of the device attach to a variety of off-the-shelf bra styles and models. Whereas, other embodiments of the device attach to bras having accommodations for the device, such as pouches to hold part or all of the device, loops to hold part of the device, or slits for part of device to pass through and be held in place with the assistance of the bra. Bras can be worn with or without the device attached.

The heart monitor device is unobtrusive under clothes and comfortable enough to be worn all day for continuous ECG monitoring. The device includes at least two ECG sensors made of comfortable materials and held in place between the bra and the user's skin. Generally the sensors are located in the area of the bra's chest band. The sensors are wired to an electronics module that includes one or more ECG amplifiers and a transmitter for wireless transmission of the ECG, heart rate, or other derived data to a nearby computing device. The heart monitor device includes a battery to power the electronics. In most embodiments the housing material is flexible to be comfortable against the body and thin to provide a low profile under or next to the bra. The device could be a flexible assembly or could have sensors attached by wires to an electronics module.

The device and bra cooperate as a system to provide ECG, with the bra providing tension to hold sensors reliably close to the skin, while providing access to those locations on the body known for high-quality ECG signal characteristics. Tension from the bra helps to keep the sensors from sliding across the surface of the skin. The device may be held in place solely by the tension of the bra or the device may include mechanisms for attachment to the bra, including, for example, a high friction material against the bra and/or the skin, hooks to hang onto the bra, or clips to attach to the bra.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 15 is view depicting lead configurations.

DETAILED DESCRIPTION OF THE PREFERRED EMBODIMENT

Figure 1:
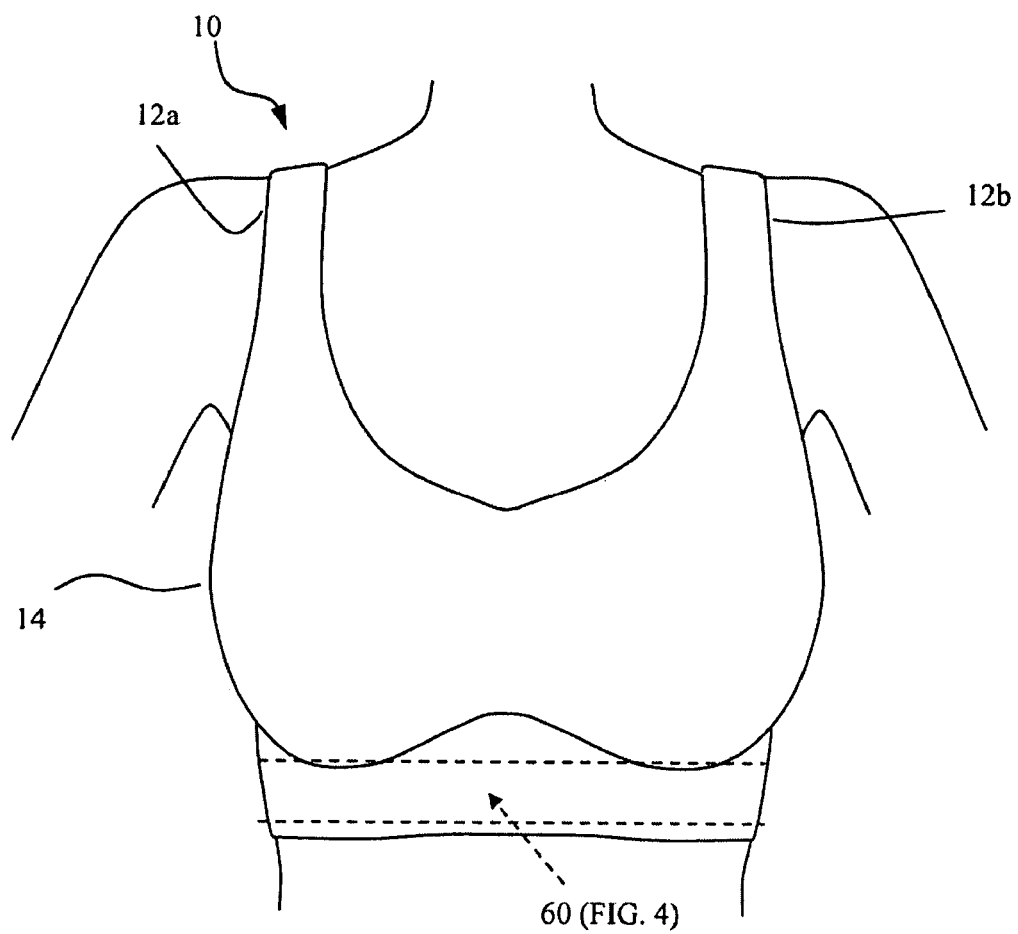
FIG. 1 is a front view of a bra on a female torso with an attachable monitor.
Figure 2:
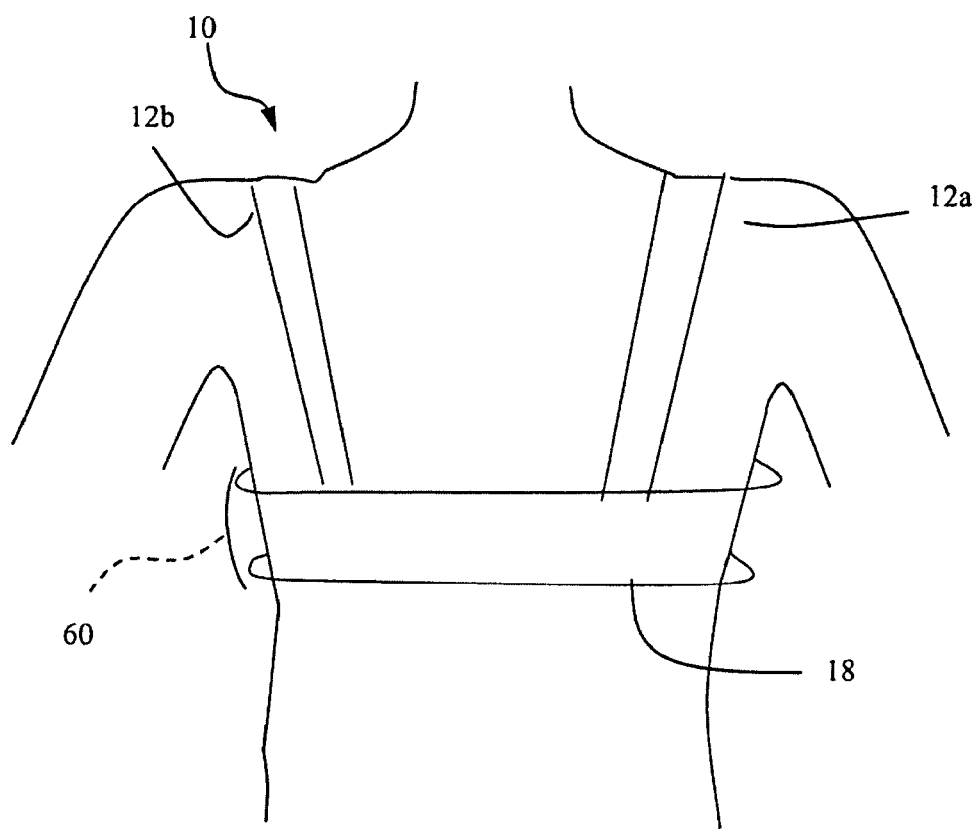
FIG. 2 is the back view of the bra of FIG. 1.

Referring to FIGS. 1 and 2, a bra 10 with a removably attached monitor device 60 carrying physiological sensors is shown. The bra 10 is shown being worn on a female subject, but the bra 10 could be worn by a male with cups appropriately dimensioned.

The bra 10 includes a front portion 14 comprising bra cups from which a pair of shoulder strap portions 12 a, 12 b emanate that rest over shoulders of the subject and terminate at a back portion 18 of the bra 10. The strap portions 12 a, 12 b extend over the shoulders and meet at the hack portion 18 that rests against the back of the subject, as shown in FIG. 2.

Figure 3:
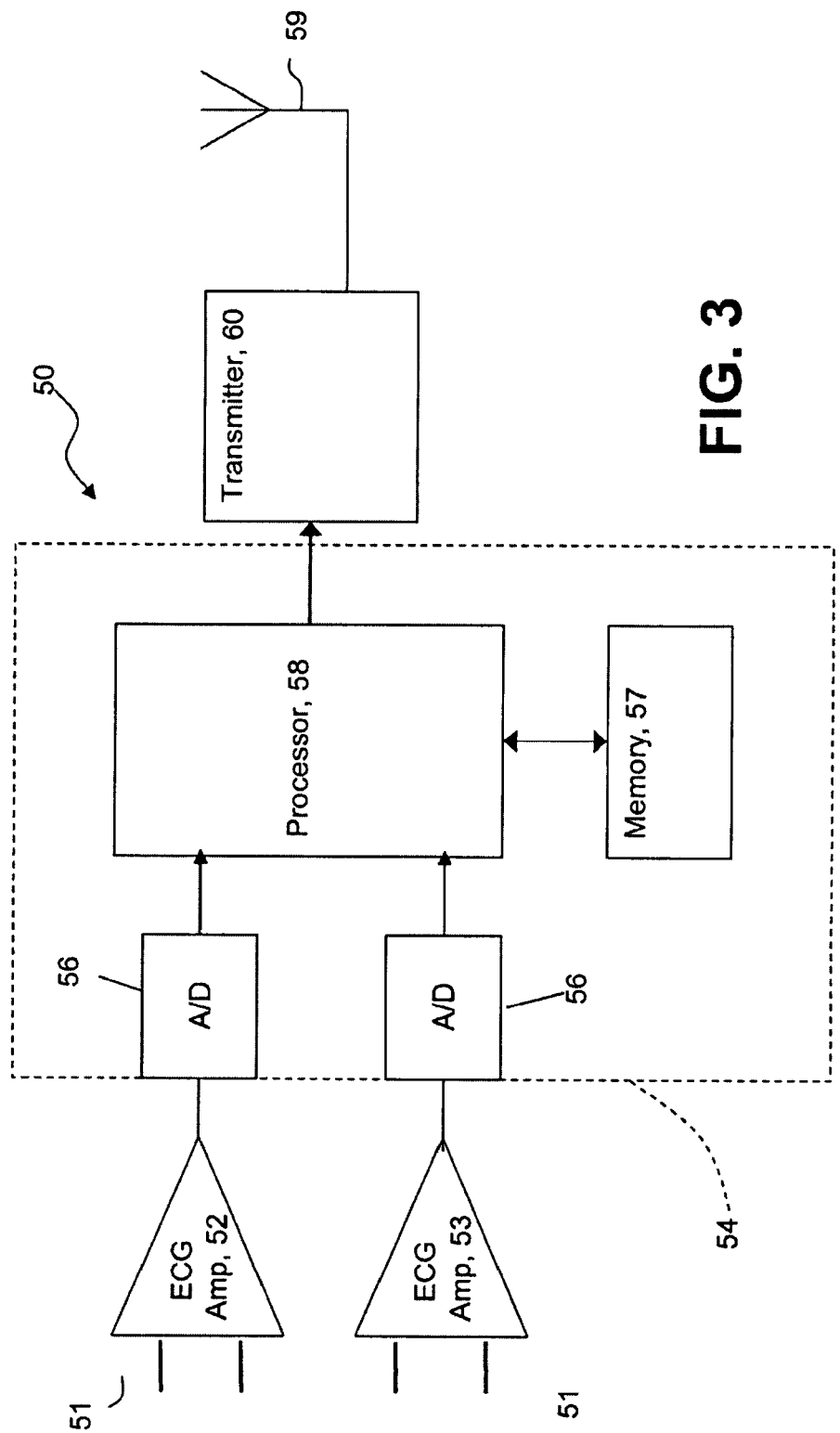
FIG. 3 is a block diagram of a typical circuit arrangement.
Figure 4:
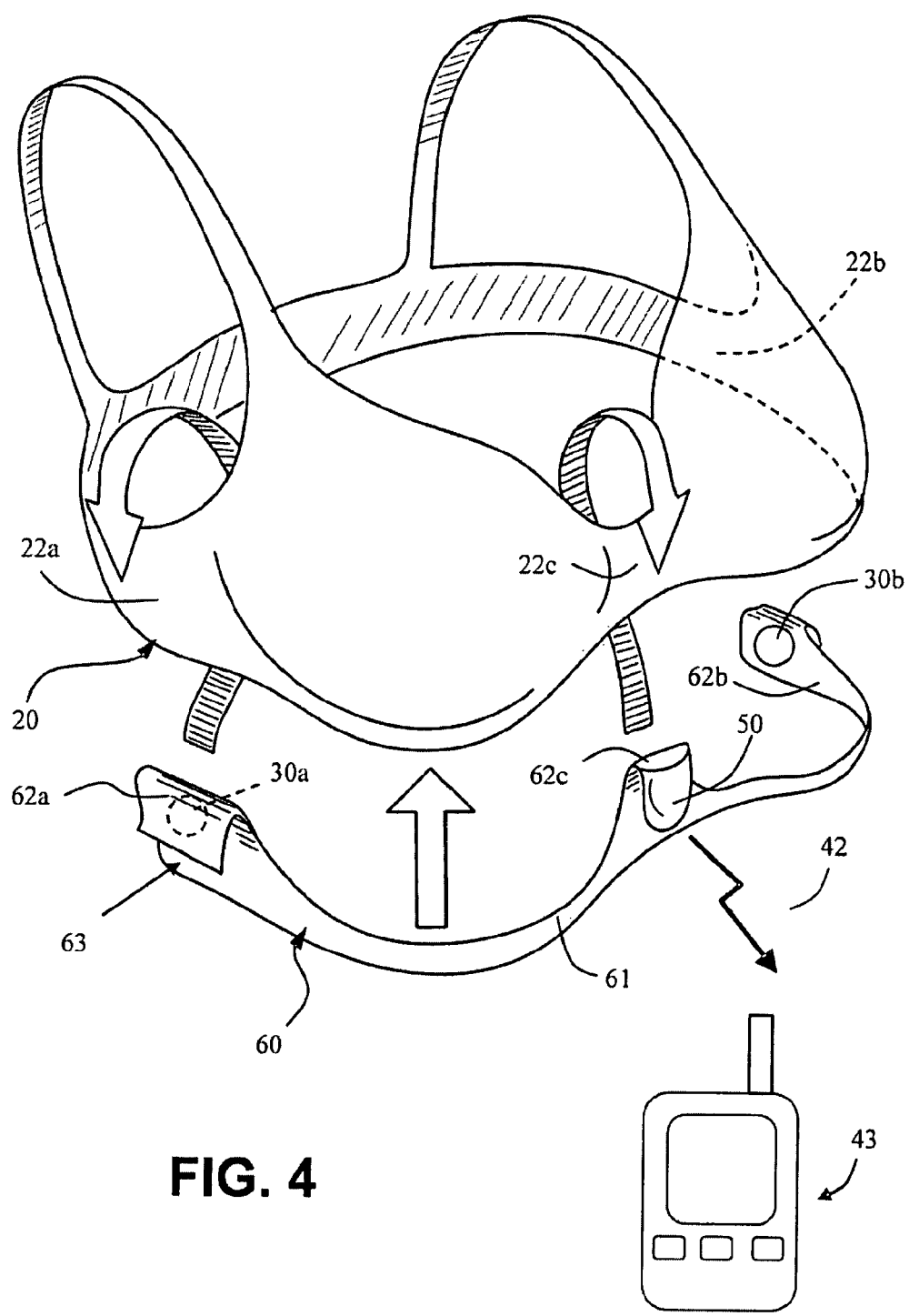
FIG. 4 is a perspective view of the bra with attachable monitor.

The bra 10 supports a plurality of sensors carried by the monitoring device 60 (FIG. 4). The monitor device 60 can also have an electronics module 50 (FIG. 3) that can wirelessly transmit signals from the sensors to a nearby computer, PDA or wireless phone. A PDA 43, as shown in FIG. 4, may be carried by the person wearing the bra 10. Although the sensors described herein will be principally ECG sensors, it is to be understood that the sensors can be any type of physiological type sensor such as motion sensors, body temperature sensors and impedance plethysmography sensors, and so forth.

Referring to FIG. 3, the electronics module 50 typically includes input connectors 51 that are connected to signal amplifiers 52-53. Each amplifier is connected to two sensors to create one ECG lead. Thus in the configuration of FIGS. 3, 4 individual sensors could be connected to the 4 inputs, or 3 sensors could be used, with one sensor connected to the input of 2 different amplifiers. For a system with two sensors, only one ECG amplifier 52 and A/D converter 56 is needed. The amplifiers receive signals from sensors, via an integrated wiring system. The signals from the sensors are amplified, and the amplified signals from these amplifiers are fed into pre-processing circuitry 54 that prepares the signals for transmission and subsequent processing.

The pre-processing circuitry 54 can include A/D converters 56 to digitize the signals from the amplifiers, and may optionally include filters to filter the signals or perform signal processing and identification of physiological conditions. The pre-processing circuitry 54 includes a memory 57 and a processor 58 to implement filtering and processing functions to provide intermediate results and to store information before transmission. Other circuitry is not shown; for instance, timing, storage, interface circuitry and so forth.

The pre-processing circuitry 54 couples the pre-processed signals to a transmitter 60 and antenna 59 that transmits the signal to a base station 43 (FIG. 4). The signal may be transmitted using, for example, Zigbee or Bluetooth protocols, to a base station that can be a computer, PDA (as in FIG. 4) or wireless phone and so forth.

An example of an electronic module is the Alive heart monitor by Alive Technologies Pty. Ltd., (International publication No. WO2005/048830). The Alive heart monitor receives an ECG signal from 2 sensors, amplifies the signal, digitizes the signal, and transmits the signal via the Bluetooth protocol.

Typically, the electronics module 50 is an integral part of the device 60. An alternative is to enclose the electronics module 50 in a case that can be removed from the device 60, and reattached using connectors 51. The electronics module is powered by a battery, which is typically removable from the electronics module 50 for replacement, but alternatively can be permanently sealed in the electronics module 50.

In some configurations, the sensors are coupled to an analog multiplexer and the output of the multiplexer can be coupled to an amplifier. In that configuration a circuit (not shown) selects which sensor to couple through the analog multiplexer.

There are several scenarios for how the monitor device might be used, including, for example, chat signals might be analyzed by the PDA/phone and transmitted to a monitoring center for analysis by a physician.

The monitoring device 60 attaches to any suitable garment that tightly encircles the torso or other parts of the body, for example, certain types of clothing for instance, a bra, or a chest strap, a tight chest harness (e.g. sports or military accessory), and so forth.

Many types of commercial and military chest harness, have characteristics to suitably hold the monitoring device 60 tightly against the skin and hold sensors in useful positions for ECG or other physiological monitoring functions, for example, mountain climbing chest harness, cave exploration chest harness, medical monitoring harness (e.g. breathing monitor), chest harness for camera, military chest harness, radio chest harness, rescue harness.

Referring to FIG. 4, a monitor device 60, i.e., a garment accessory, which is attachable to an article of clothing such as a conventional bra 20, is shown. The monitor device 60 is configured to attach to a variety of off-the-shelf articles of clothing such as a chest strap or a bra. Attached to a bra 20 of the basic type shown in FIG. 4, the bra 20 does not need any modifications to work with the device 60. Other embodiments that work with modified bras 20 are discussed below.

The monitor device 60 is comprised of a thin, firm, flexible band 61 of material that may be similar to, for example, flexible printed circuit material, such as that used for circuit cables in computers. In this particular embodiment, the monitor device 60 is in a shape that conforms to the front bottom portion of the bra 20, at the lower portion of the bra cups (not numbered), allowing the band 61 of thin material of the monitor device 60 to comfortably slip underneath the front bottom portion of the bra 20.

The monitor device 60 includes a fastener mechanism, e.g., a tab 62 a on the user's right side that is folded over to form a hook portion 63 that bends away from the user's body. The tab 62 a is comprised of a relatively stiff material to maintain the hook shape of the folded tab. The folded tab 62 a hooks over the bra 20 on the bra's right side strap 22 a. Similarly, the device's left tab 62 b hooks over the bra's left side strap 22 b. The monitoring device 60 also has a center tab 62 c configured to hook over a central portion 22 c of the bra 20 (e.g., in the area of the bra between the two bra cups).

The monitoring device 60 includes sensors 30 a and 30 b on the side of the device facing the user (the "skin side"). ECG sensor 30 a is on the skin side of tab 62 a and ECG sensor 30 b is on the skin side of tab 62 b. The sensors 30 a, 30 b are connected by wires (not shown) to an electronics module 50 which includes an amplifier and wireless transmitter, as discussed above. The electronics module 50 is preferably located at the center tab 62 c. The wires are integrated into monitoring device 60 to run through the body of the device 61, preferably using flexible circuit material. Alternative arrangements for sensors and electronics module 50 are possible. For instance, sensors could be located anywhere on the skin side of the band 61 of monitoring device 60.

The heart monitor device 60 uses the module 50 to transmit data 42 to a nearby computer, PDA 43 or wireless phone carried by the person wearing the device 20.

Figure 5:
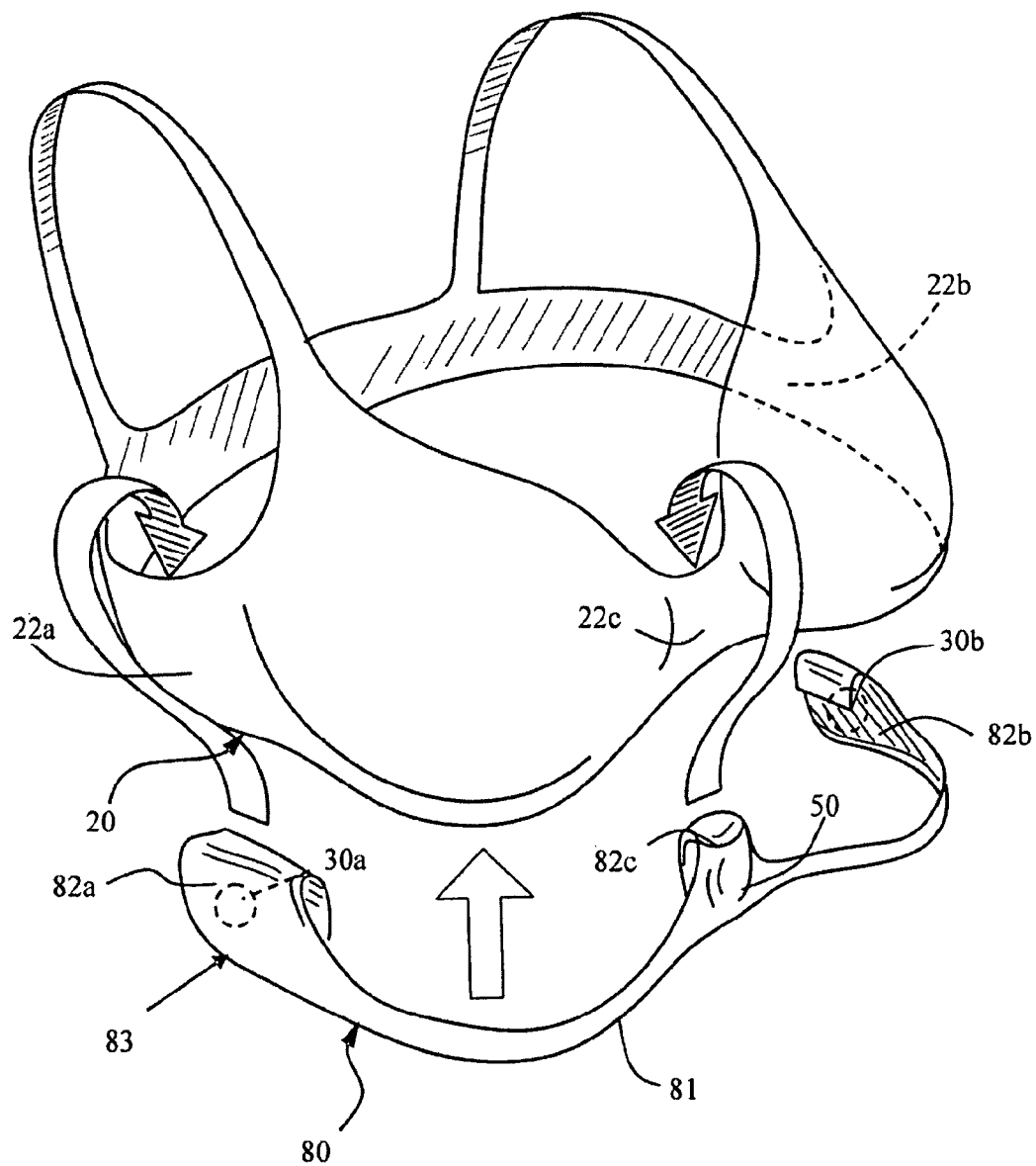
FIG. 5 is a perspective view of a bra with an alternative attachable monitor.

Referring now to FIG. 5, an alternative monitoring device 80, a variation of monitoring device 60 in FIG. 4 is shown. The monitoring device 80 is arranged to be worn outside of the bra 20. Again other types of clothing could be used instead of the bra. Depending on the underlying bra type, this embodiment may be more easily attachable to certain bras or may be more comfortable than monitoring device 60. When the user is already wearing the bra, it may be easier to attach monitoring device 80 than to attach monitoring device 60 which is slid underneath the bra cups.

The monitor device 80 is comprised of a thin, firm, flexible band 81 of material that may be similar to, for example, flexible printed circuit material, as mentioned above. In this particular embodiment, the monitor device 80 includes a fastener mechanism, e.g., a tab 82 a on the user's right side that folds over inwards toward the user's body to form a hook portion 83 bending inwards (opposite to that of FIG. 4). As with the monitoring device 60, the tab 82 a is comprised of a relatively stiff material to maintain the hook shape of the folded tab. The folded tab 82 a hooks over the bra 20 on the bra's right side strap 22 a and a similar arrangement of a left tab 82 b hooks is provided for the bra's left side scrap 22 b. The monitoring device 80 also has a center tab 82 c configured to hook over a central portion 22 c of the bra 20 (e.g., in the area of the bra between the two bra cups).

In addition, the monitoring device 80 includes sensors 30 a and 30 b on the side of the device facing the user (the "skin side"). ECG sensor 30 a is on the skin side of tab 82 a and BCG sensor 30 b is on the skin side of tab 82 b. The sensors 30 a, 30 b are connected by wires (not shown) to an electronics module, as discussed above.

Figure 6:
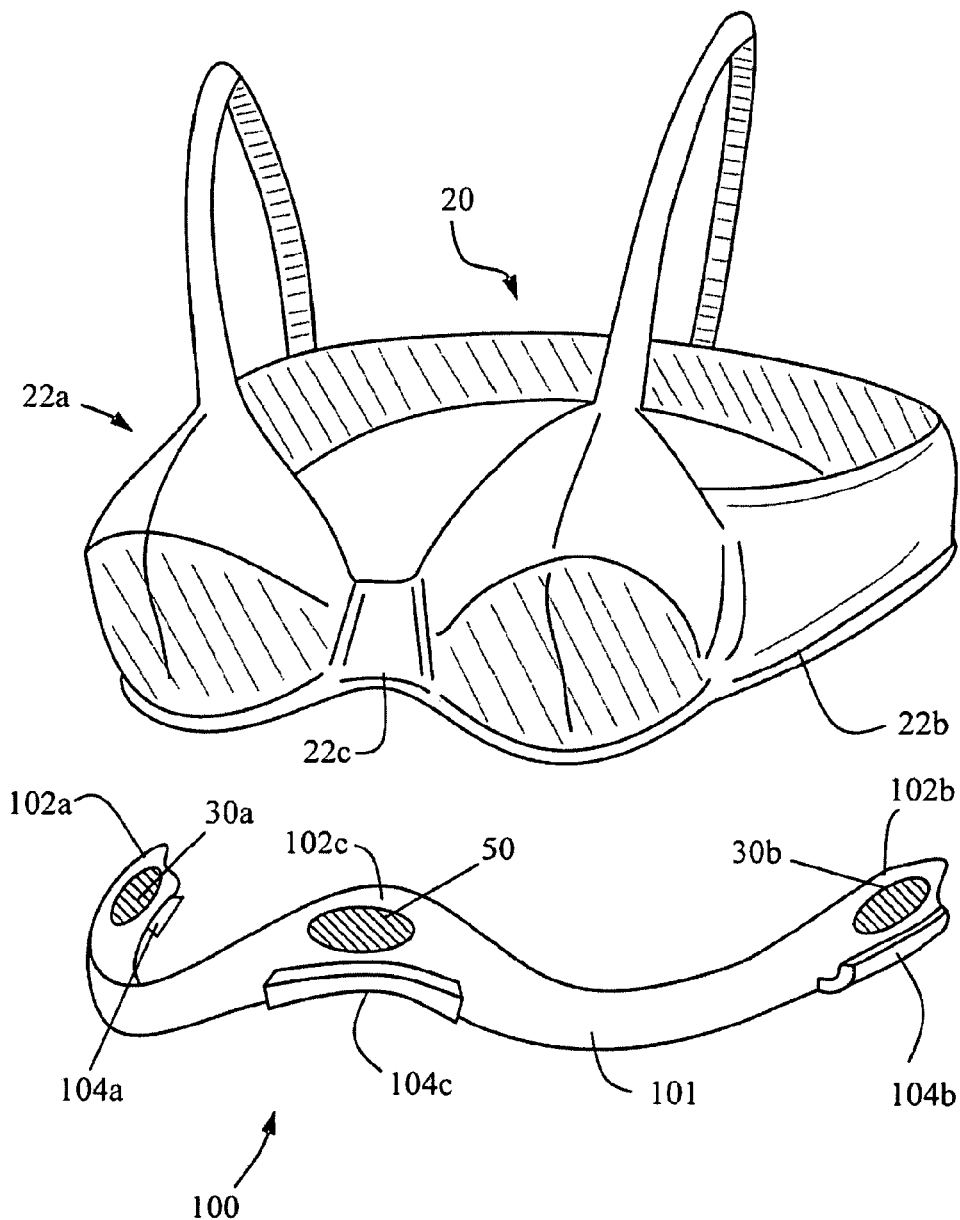
FIG. 6 is a perspective view of a bra with another attachable monitor.

Referring to FIG. 6, another variation 100 of a monitoring device that attaches to a bra is shown. In this variation, a clip mechanism is used to attach the monitoring device 100 to the bra 20, rather than use hooked tabs and gravity, as above. The monitoring device 100 is similar to those discussed in FIG. 4 in that the monitoring device 100 is shaped to conform to the front bottom portion of the bra 20, at the lower portion of the bra cups, and is comprised of a thin flexible, e.g., circuit board material, allowing monitoring device 100 to comfortably slip underneath the front bottom portion of the bra 20.

The device 100 has one end 102 a that is held between the bra's right side strap 22 a and the user's skin. At the right end 102 a, a sensor 30 a is integrated into the device. The other end of the device 202 b is held under the bra's left side strap 22 b and has a sensor 30 b. The device 100 also has a central portion 102 c that is secured under the bra's center 22 c (the area of the bra between the two bra cups). The electronics module 50 is shown in this central portion 102 c, although the sensors and electronics module could be at any location in the device 100.

The monitoring device has attachment mechanisms 104 a-104 c on the outside of the device 100 (e.g., clips or anchors) that attach to the bra.

Figure 7:
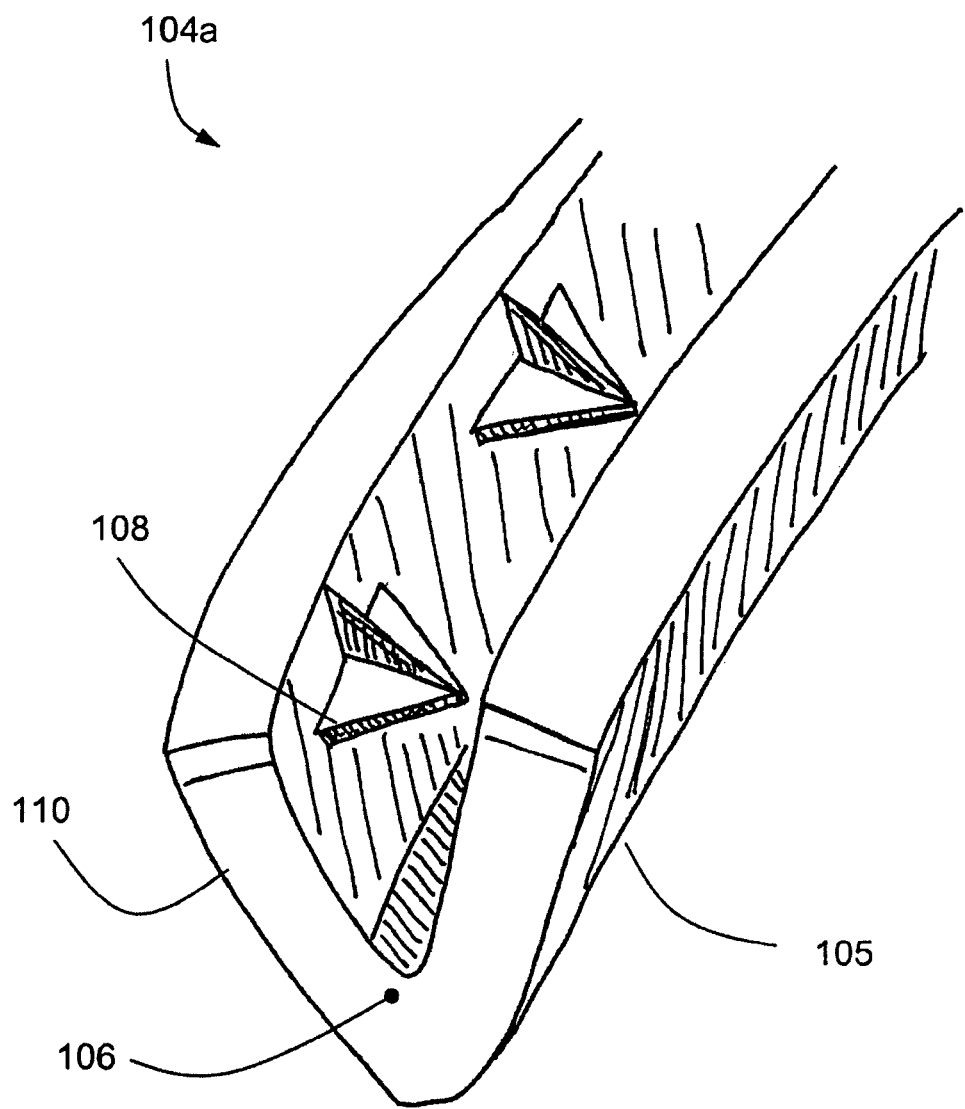
FIG. 7 is a perspective view of an attachment mechanism.

Referring now to FIG. 7, a detail of one embodiment of the attachment mechanism 104 a-104 c is shown. The mechanism 104 a has a side 105 that attaches to the outside of the device 100. It is comprised of a plastic material that generally holds its shape but is flexible. The mechanism 104 a is shaped to form a trough 106 that is large enough to accept the bottom seam of a bra. Inside the trough 106 are teeth 103 that are attached to the outer portion 110 of the mechanism. To attach the device 100 to the bra 20, the bra 20 is pulled into the trough 106. The trough 106 expands somewhat when the bra 20 is being inserted, because of the flexible nature of the mechanism 104 a. A bra seam (not shown) of the bra 20 is pulled past the teeth 108 to hold the bra within the trough 106.

Figure 8:
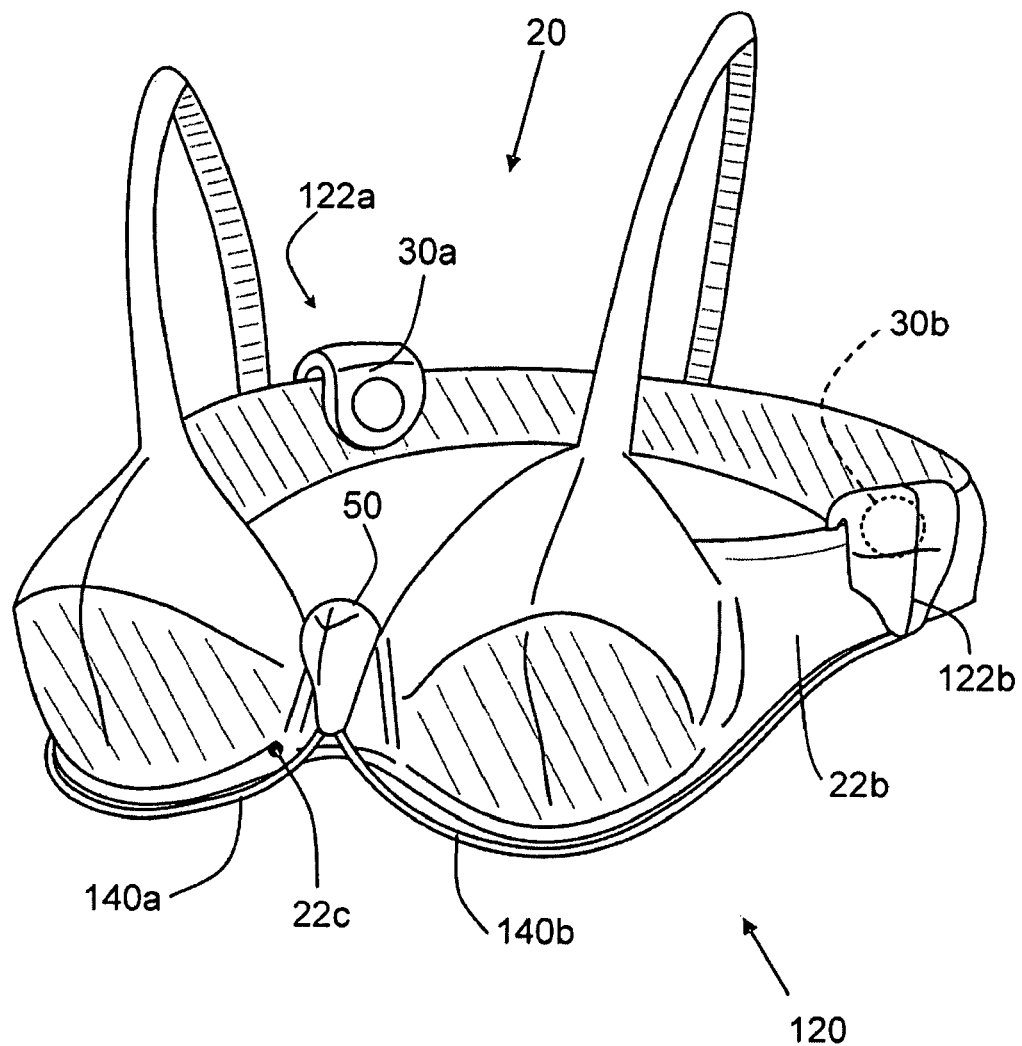
FIG. 8 is a perspective view of a bra with clip-on sensors.

Referring to FIG. 8, an alternative design 120 for the heart monitor is shown attached to a bra 20. The device 120 has an electronics module 50 that attaches to the central portion 22 c of the bra 20 (between the two bra cups). The electronics module 50 is attached to two sensor assemblies 122 a and 122 b via wires 140 a and 140 b respectively. The wires can be shielded for electromagnetic interference. The shielding can extend to the sensor assembly. Sensor assembly 122 a is shown worn on the user's back in a position for ischemia detection. On the skin side of the sensor assemblies is a wearable sensor: sensor assembly 122 b having wearable sensor 30 b.

The wires 140 a and 140 b could be permanently attached to the electronics module 50 and sensor assemblies or could have connectors such as a clip to attach to the sensor. For example, a removable connector on the sensor assemblies could accommodate different sensor assemblies for different activities. The electronics module could be attached to different locations than the one shown, for example, to the back of the bra or to the waistband of pants.

The sensor assemblies 122 a and 122 b could be attached to the bra straps 22 a, 22 b by a number of mechanisms, including a snap hinge that applies pressure to the bra strap and prevents the sensor from slipping off the bra strap; or the sensor assembly could be provided with teeth next to the bra strap to hold it in place. In addition, an elastic strap around the bra strap which attaches back to the assembly, Velcro straps, clips or other mechanisms could be used to hold the assembly in place on the bra strap.

A number of different sensor configurations are possible. For example, a sensor could be on the skin side of the electronics module 50. This sensor could take the place of the sensor on the user's right bra strap or could be used as an additional sensor. Sensors could be placed at different places on the bra 20.

The wires can be loosely coupled to the bra or wire guides can be provided in the bottom of the bra to hold the wires comfortably in place. The wire guides could be slots to hold the wires in place. Additionally, the bra could have clips to affix the wires to the bra. A bra could be provided with other accommodations for a removably attachable heart monitor device, as will be discussed below in FIG. 10.

The devices 60 (FIG. 4), 80 (FIG. 5), and 100 (FIG. 6) are shown as single unitary solid devices, with the sensors, electronics module and wiring being part of one solid assembly. Each aspect (sensors, electronics, wiring) could be a permanent part of the assembly 60, 80, 100. Similarly for device 120 (FIG. 8), the two sensors and the electronics module could each be unitary solid devices (as shown), permanently attached by the insulated wires to each other. Another option is to have some portion of the device 60, 80, 100, 120 removable and/or disposable, such as the electronics module, battery, or sensors. For example, having removable sensors would allow different types of sensors to be used for different activities. Exercise generates a lot of sweat, and desk work does not, so different sensor designs could be used depending on the anticipated level of perspiration.

Figure 9:
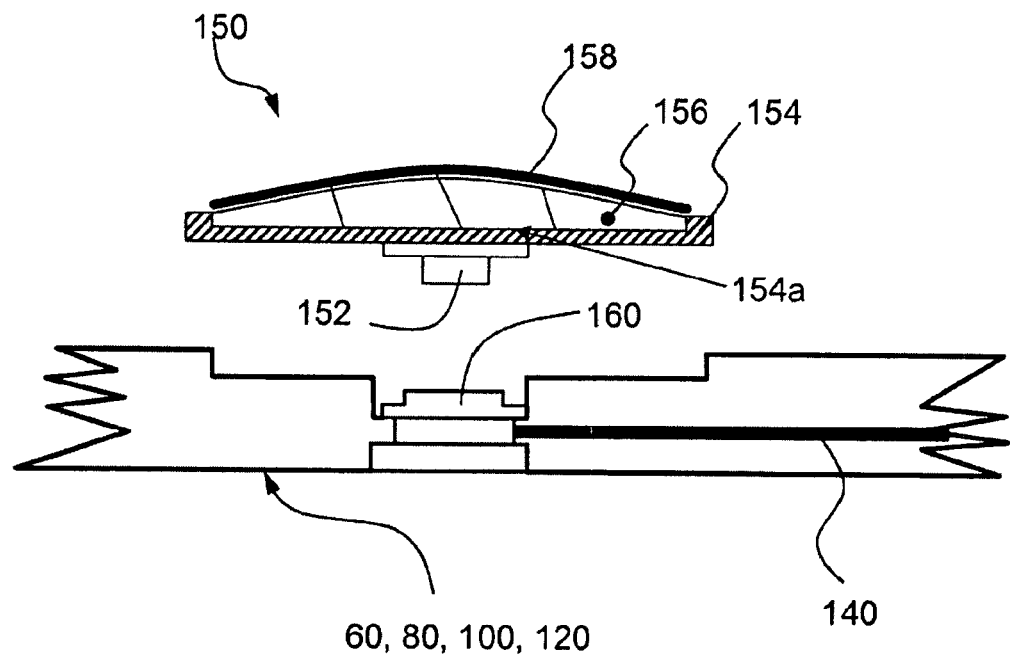
FIGS. 9-12 are cross-sectional views of removable sensors.

Referring to FIG. 9, a removable sensor 150 for sensing voltages from the skin to provide a signal for EGG monitoring is shown disposed in a portion of a monitor device 60 (FIG. 4), a monitor device 80 (FIG. 5), a monitor device 100 (FIG. 6) or a monitor device 120 (FIG. 8).

The removable sensor 150 has a snap 152. The snap 152 is attached to a sensor frame or housing 154 that is comprised of a firm but flexible material (e.g., rubber). The housing 154 is used to support a more flimsy, e.g. compliant low Young's modulus material that provides a sensor membrane 156. The sensing membrane 156 is comprised of an electrically conductive and flexible material, e.g., a conductive rubber or conductive silicone and is disposed inside the housing 154 and has a major surface thereof that is exposed so that the sensing membrane 156 can make contact with the skin. The sensing membrane 156 can be a flat or curved surface, as shown, to ensure secure and adequate contact with the skin.

The sensing membrane 156 may be temporarily covered with a conductive gel or a hydrogel film 158. A thin hydrogen film could be cut to size, and would provide excellent skin conduction to a wearable sensor material such as conductive silicone. Hydrogel, however, is not very durable and so the hydrogel might be used for, e.g., a day and then discarded and replaced.

The snap 152 is comprised of an electrically conductive material, e.g., a metal, conductive plastic, or hard conductive rubber and is disposed in intimate contact with the backside of the sensing membrane 156 to provide an electrical path for a signal from the sensing membrane 156 to a mating snap 160 on the device 60, 80, 100, or 120. This contact can be provided either by having the membrane 156 in intimate contact with a conductive back portion 154 a of housing 154 or through an aperture (not shown) in the back portion 154 a of the housing 154 that allows the snap 152 to be directly and electrically connected to the membrane 156.

The device 60, 80, 100, or 120 in this example would have an accommodation for the sensor 150. Here the accommodation is a mating snap 160. The removable sensor 150 thus attaches to the device by mating the snap 152 on the sensor 150 with the corresponding mating snap 160 on the device. In this configuration a wire 140 would be coupled to the mating snap 160 to carry the electrical signal to the electrical circuitry (FIG. 3). The snap 160 attaches to the device 60, 80, 100, or 120 by being disposed through an aperture in the material and crimped to surrounding material of the or device to hold the snap 160 in place.

The conductive snap arrangement just described could also be used to attach an aspect of a removable electronics module 50 to a device 60, 80, 100, or 120. Other attachment mechanisms can be used for those aspects that require electrical connectivity, for example, conductive Velcro or other hook and loop type fastener mechanisms could be used instead of a conductive snap.

Thus, sensors could be permanently attached to the heart monitor device, or could be removable. Parts or all of a removable sensor could be disposable (e.g. the hydrogel membrane).

A bra 10, 20 could be provided with accommodations for a removably attachable heart monitor device, including pockets, loops of material, slits and accommodations briefly mentioned above, which would help attach the heart monitor 60, 80, 100, 120 to the bra 10, 20, holding the heart monitor securely in place. Accommodations such as pockets, loops of material, slits and clips would allow the bra to be comfortably worn with or without the attachable heart monitor. The bra's accommodations could accommodate any aspect of the heart monitor 60, 80, 100, 120, that is, any portion could thread through the loop of material to be securely held in place, for example. The portion of the device that fits in the accommodation may be a section of the device assembly that includes the electronics module, wiring or sensors. As an example, referring back to FIG. 6, the bra 20 could be fashioned with pockets for the device 100, to hold the ends 102 a and 102 b, as an alternative to or an additional attachment mechanism to the clips 104 a-104 c. As another example, a bra accommodation such as a pocket in a bra 10, 20 may be especially useful to place and hold a sensor assembly in locations on the body that are known for quality ECG sensing. The face of the sensor can make contact with the skin of the user or alternatively capacitive-coupled sensors could be used.

Figure 10:
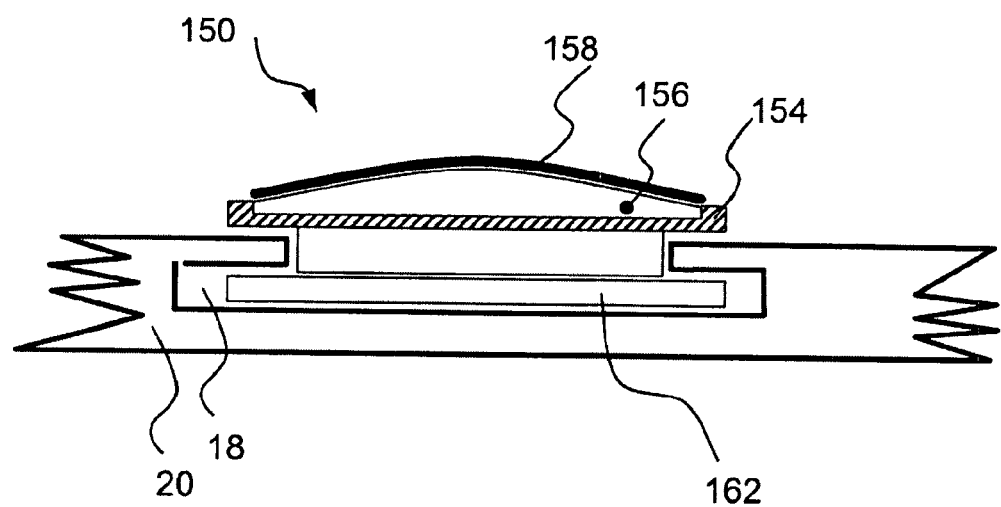

Referring to FIG. 10, an example of a bra 20 accommodation is shown. The bra 20 includes a pocket 18 (or a pouch or opening) to accommodate a sensor assembly 150 which is shaped to fit in the pocket. The pocket 18 is located in the side strap of the bra. Other locations in the bra or garment are possible. The pocket 18 is provided in the garment that is comprised of two layers of material. The sensor assembly 150 is shaped so that the bottom of the sensor assembly 162 fits in the pocket 18. The sensor assembly 150 may fit snuggly in the pocket 18, in which case the bra would provide the function of holding the sensor in place. Alternatively, the sensor assembly 150 could fit loosely in the pocket 18, with the bottom of the sensor assembly 150 preferably being coated with a low-friction material like Teflon, allowing the bra to move and stretch. The face of the sensor 150 would preferably be a high friction material to hold the sensor against the skin.

Figure 11:
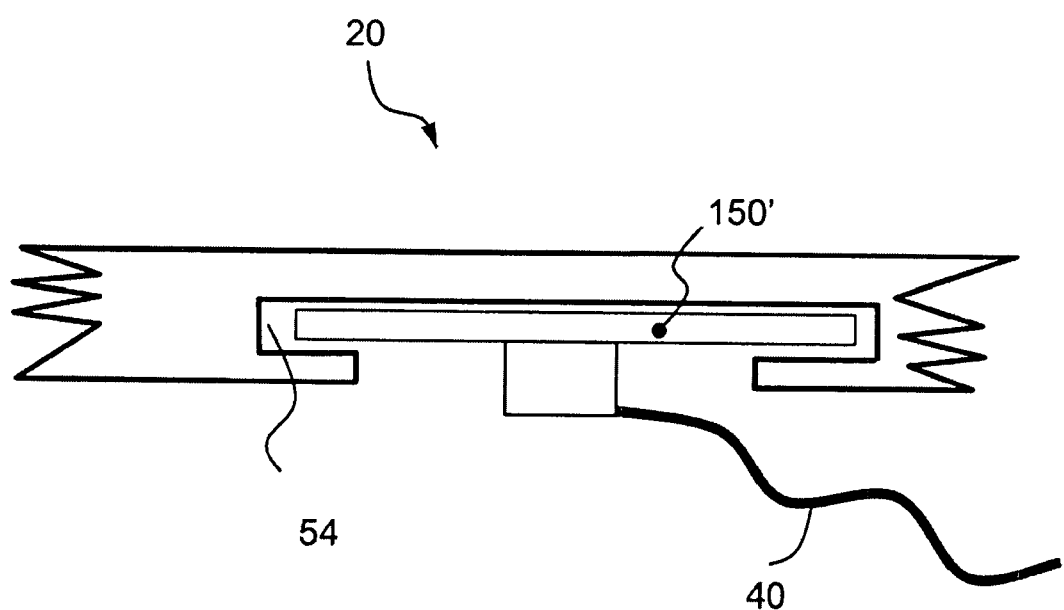

Referring to FIG. 11, an example of an arrangement with a sensor 150' that does not need direct skin contact, such as a capacitively coupled sensor for measuring ECG is shown. These types of sensors 150' could slip into a pocket 54 on the outside of the bra 20 and would not need to be in direct contact with the skin of the subject.

The heart monitor device is designed to place ECG sensors at physiologically interesting and useful places. The device can also hold other types of sensors, some of which can be of use in interpreting or processing the ECG signal. The device could incorporate motion sensors: detected motion can be used, for example, to invalidate portions of time in the ECG signal from a nearby ECG sensor when a large amount of motion is detected. ECG sensors can be used in conjunction with impedance plethysmography sensors to measure cardiac output. Sensors to measure surface skin temperature may add to the overall measure of user health.

The ECG sensors can be provided with a sensing material comprised of metal such as a conventional silver/silver chloride compound. While this metal material could be used, the metal material is somewhat inflexible, does not naturally stick to the skin, and can become slippery in the presence of perspiration. Other materials can be used such as conductive silicone, a wearable material commonly used for shock therapy electrodes, or conductive rubber provided by adding conductive, skin-friendly materials such as silver, gold or carbon to liquid rubber and molding the composition into the desired shape of a sensor. Other conductive materials such as conductive fabric provided by weaving fine threads of silver together with conventional fabric threads; or coating fabric threads with metal can be used.

Hydrogels can be used as a thin layer between any of these wearable sensor materials and the skin, as previously mentioned. These materials are suitable for sensing ECG signals from the skin without any skin preparation. The shape of the sensor can help maintain contact with the skin.

FIGS. 3 and 10 depict a smooth rounded sensor that would gently push against the skin to make contact with the skin of a subject.

Figure 12:
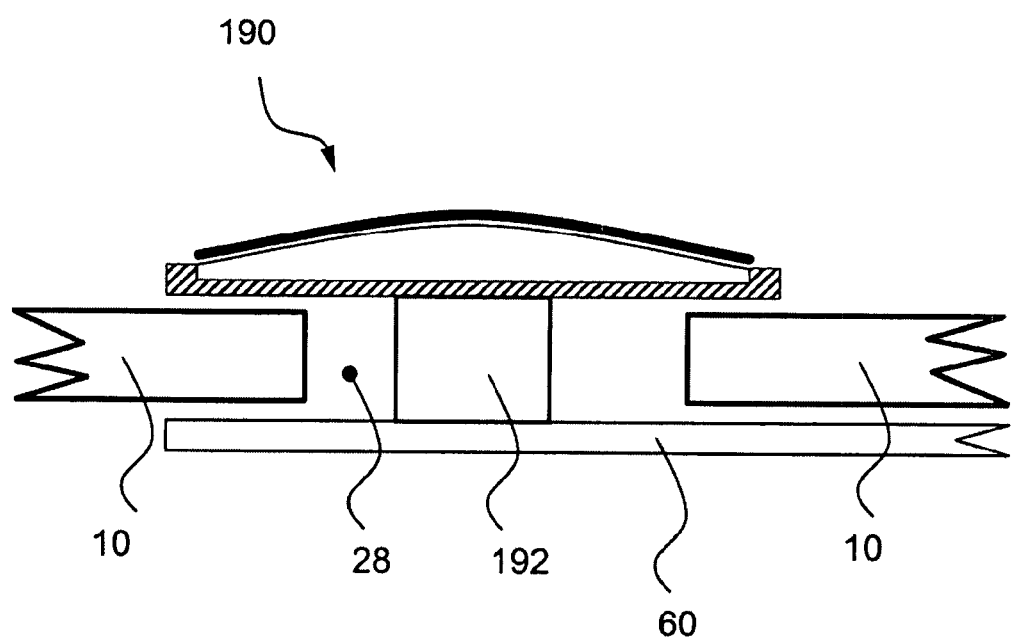

Referring to FIG. 12, a variation of the heart monitor device has sensors 190 configured with the structure of buttons, such that the button sensors can be slipped through slits 28 (like buttonholes) in some portion of the bra 10, for example, the chest band portion of a bra 10 such as that pictured in FIG. 1. The slit 28 allows a button sensor 190 to touch the skin, and also holds the sensor in place. For a suitable bra, adding these buttonholes is a very simple modification. The sensor 190 has a post 192 attached to the bottom of the sensor, which fits through the slit 28 in the bra 10 chest band. The post 192 is connected to the heart monitor device, e.g. 60 and the button hole in the chest band slips over the sensor and post.

Figure 13A:
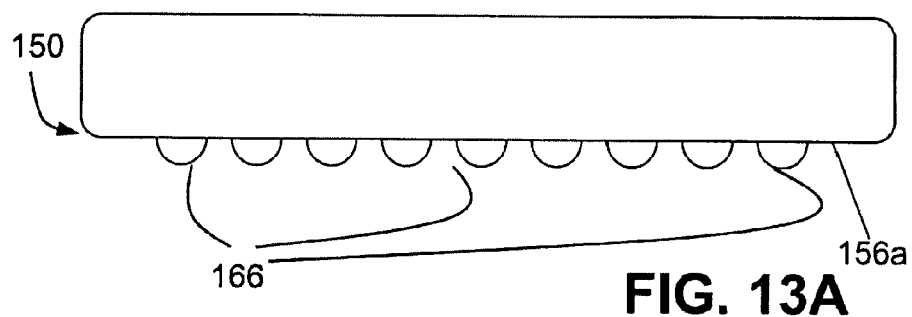
FIGS. 13A-13D are cross-sectional views showing possible surface preparation for sensor membranes.

FIGS. 13A-13D shows cross sections of sensor faces showing different textures. In FIG. 13A, the sensor 150 has a sensor face 156 *a* with nubs or bumps 166 shaped like gumdrops on the surface of the sensor that touches the skin. This configuration of the surface would be suitable for working around body hair, as the nubs would have a good chance of pressing in between the hairs to reach the skin. Excessive sweat could also be channeled between the nubs 166.

Figure 13B:
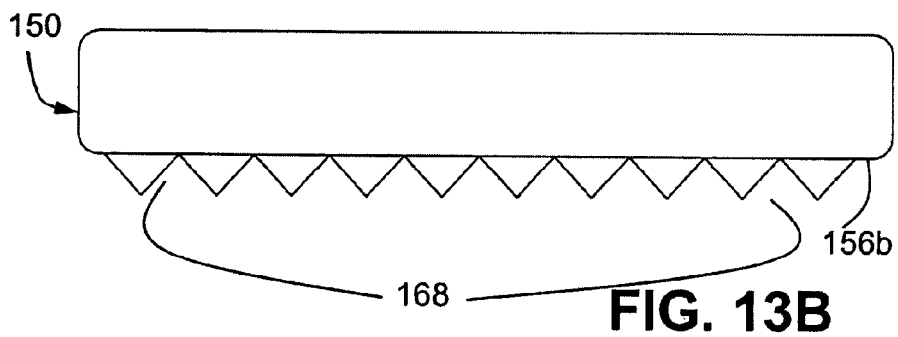

FIG. 13B shows a sensor face 156 *b* having sharp ridges 168 which may be more suitable for reaching the skin through hair, than the nubs 166 of FIG. 13A. Sweat could also be channeled through the grooves in between the ridges 166.

Figure 13C:
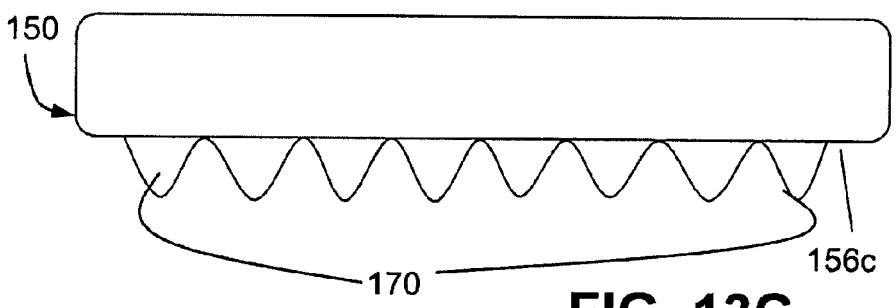
Figure 13D:
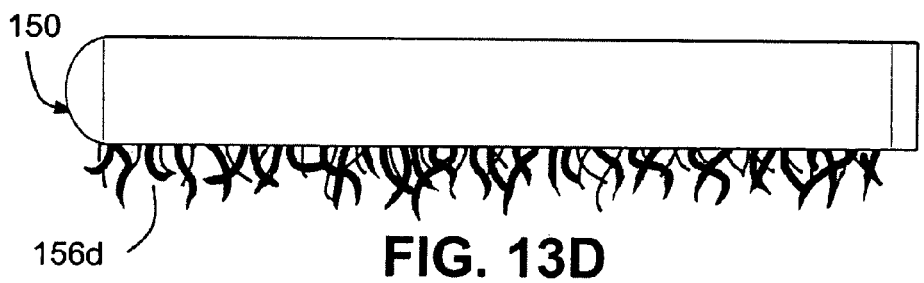

FIG. 13C shows another variation with grooves cut into the sensor face 156 *c* forming softer ridges 170. In FIG. 13D conductive threads 156 *d* are provided in the sensor face and help maintain contact with the skin even when the sensor is sliding across the surface of the skin.

Figure 14A:
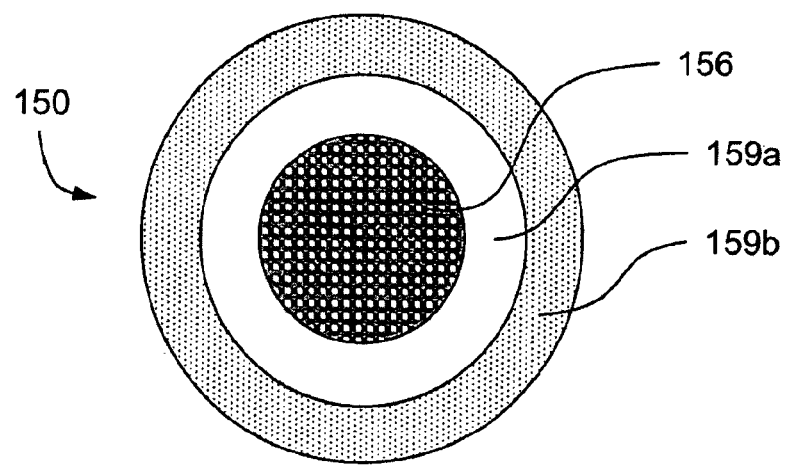
FIGS. 14A and 14B are plan and cross-sectional views of an alternative sensor.
Figure 14B:
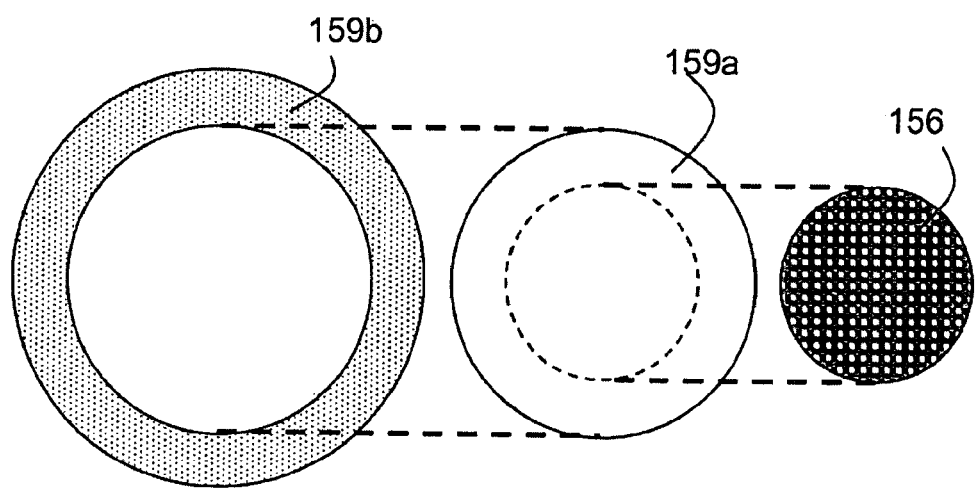

Referring to FIG. 14, to prevent the sensor 150 from sliding, a ring of sticky or high-friction material 159 *a* such as rubber or soft silicone could foe placed around the sensing material 156. The friction ring 159 *a* may be made of waterproof material (silicone, for example), which may also induce sweat.

Sweat is a good conductor for ECG sensors, and inducing a little sweat can help maintain skin contact and conductivity. However, if there is too much sweat, the sensor may slide against the skin, inducing noise in the signal, and the excess sweat may be uncomfortable. For this reason it may be beneficial to have a sweat absorbing ring 159 *b* that surrounds the rest of the sensor. The sweat-absorbing material 155 *b* can be made of cotton, for example.

The sensing material may be in the shape of a flat disk, as shown in FIG. 14A, and made of a conductive fabric which can absorb some sweat. These conductive fabrics tend to dry out when the user is not perspiring, which may drastically reduce the sensor's conductivity. One solution is to apply a waterproof or water resistant backing 159 *a* to the sensing material 156, to help keep the sensing material 156 damp by sweat. The material 159 *a* extends beyond the edges of the sensing material 156 to make contact with the skin and provide the high-friction function, while also providing a water resistant barrier around the sensing material 156 to induce sweat. For applications where large amounts of sweat are anticipated, the sweat disk 159 *a* could be constructed of water resistant material that allows some evaporation. The sweat-absorbing ring 159 *b* is shown in FIG. 15B does not overlap any other part of the sensor, but is a separate ring to ensure direct shin contact and prevent sweat from dripping down from the sensor.

The sensing material 156, friction ring 159 *a* and sweat-absorbing ring 159 *b* are shown as circular shapes. However, these elements could be rectangular or any other shape or provided in alternating strips, and still provide the same functions.

The ideal physiological sensor would be able to induce enough sweat for good conduction, but wick away excess sweat. In the absence of the ideal, users may desire to have different sensors for different activities, different amounts of sweat, and differences in comfort. Users may differ in how dry their skin is, how much body hair they have, or how much they sweat, requiring different sensors. To work in the presence of sweat or hair, an uneven surface will allow parts of the sensor to reach the skin and make good contact.

The devices 60, 80, 100, or 120 carry comfortable sensors that need not use adhesive against the skin and can stay in place against the skin. The mechanisms that hold the sensors against the skin include a tensile force that is imparted to the sensors by the bra 20. Also, in some embodiments, the sensors will tend to stay in place against the body by providing the sensor faces with a relatively high-friction surface to minimize slippage against the skin. The bra 20 allows sensors to be placed at physiologically useful places on the body. In some embodiments, the sensors may also have slightly sticky or tacky surface to help to hold the sensors in place against the skin.

Referring now to FIG. 15, there are several possible ECG lead configurations with the attachable heart monitor 60, 80, 100, or 120. Using ECG sensors at the position of V6 and V6R, a lead from V6 to V6R will provide ECG with good amplitude. V6 to V2 would also be good, and adding a ground sensor at V6R would help signal stability. Additional leads could use sensors at V3, V4 and V5, which are very close to the heart and provide good amplitude. A sensor on the back chest band of the bra may provide information about ST changes in the ECG over time, which can be an indication of myocardial ischemia.

A number of embodiments of the invention have been described. Nevertheless, it will be understood that various modifications may be made without departing from the spirit and scope of the invention.

What is claimed is:

1. A brassiere comprising:
   at least one accommodation disposed on a portion of the brassiere, the at least one accommodation configured to carry a sensor; and the sensor, the sensor being detachably carried by the at least one accommodation;
wherein the at least one accommodation further comprises a first layer of material with a first aperture and a second layer of material disposed behind the first layer of material;
wherein the sensor further comprises a sensor face having a sensor face width and a bottom having a bottom width attached to each other by a midsection having a midsection width smaller than the bottom width; and
wherein the bottom is coated with a low friction material.

2. The brassiere of claim 1 wherein the sensor is at least one of an ECG sensor, a motion sensor, a body temperature sensor, or an impedance plethysmography sensor.

3. The brassiere of claim 1 wherein the sensor includes a sensor membrane configured to rest against skin of a wearer of the brassiere; wherein the sensor membrane comprises an electrically conductive, flexible material.

4. The brassiere of claim 3 wherein the sensor membrane has a major surface that is exposed to make contact with the skin of the wearer of the brassiere; and wherein the major surface is curved or flat.

5. The brassiere of claim 4 wherein the major surface of the sensor membrane is covered with a conductive gel film.

6. The brassiere of claim 3 wherein the sensor further comprises a sensor frame comprised of a firm, flexible material supporting the sensor membrane.

7. The brassiere of claim 3 wherein the sensor membrane comprises a water resistant material to induce sweat.

8. A brassiere comprising:
at least one accommodation disposed on a portion of the brassiere, the at least one accommodation configured to carry sensor; and
the sensor, the sensor being detachably carried by the at least one accommodation;
wherein the at least one accommodation further comprises a first layer of material with a first aperture having an aperture width and a second layer of material disposed behind the first layer of material;
wherein the sensor further comprises a sensor bottom coated with a low friction material; and
wherein the sensor further comprises a sensor face having a sensor face width larger than the aperture width.

9. The brassiere according to claim 1 wherein the first layer of material is affixed to the second layer of material around the aperture.

10. The brassiere according to claim 1 wherein the sensor face is coated with a high friction material.

11. The brassiere of claim 9 wherein the sensor is at least one of an ECG sensor, a motion sensor, a body temperature sensor, or an impedance plethysmography sensor.

12. The brassiere of claim 9 wherein the sensor includes a sensor membrane configured to rest against skin of a wearer of the brassiere; wherein the sensor membrane comprises an electrically conductive, flexible material.

13. The brassiere of claim 12 wherein the sensor membrane has a major surface that is exposed to make contact with the skin of the wearer of the brassiere; and wherein the major surface is curved or flat.

14. The brassiere of claim 13 wherein the major surface of the sensor membrane is covered with a conductive gel film.

15. The brassiere of claim 12 wherein the sensor further comprises a sensor frame comprised of a firm, flexible material supporting the sensor membrane.

16. The brassiere of claim 12 wherein the sensor membrane comprises a water resistant material to induce sweat.

17. The brassiere according to claim 9 wherein the first layer of material is affixed to the second layer of material around the aperture.

18. The brassiere according to claim 9 wherein the sensor face is coated with a high friction material.

\* \* \* \* \*